(12) United States Patent
Babin et al.

(10) Patent No.: US 6,762,829 B2
(45) Date of Patent: Jul. 13, 2004

(54) MEASUREMENT OF OPTICAL PROPERTIES OF PASSIVE OPTICAL DEVICES USING THE MATRIX METHOD

(75) Inventors: François Babin, Charlesbourg (CA); Normand Cyr, Sainte-Foy (CA)

(73) Assignee: EXFO Electro-Optical Engineering Inc., Vanier (CA)

( * ) Notice: Subject to any disclaimer, the term of this patent is extended or adjusted under 35 U.S.C. 154(b) by 0 days.

(21) Appl. No.: 10/373,736

(22) Filed: Feb. 27, 2003

(65) Prior Publication Data

US 2003/0160951 A1 Aug. 28, 2003

Related U.S. Application Data

(60) Provisional application No. 60/359,647, filed on Feb. 27, 2002.

(51) Int. Cl.[7] .............................................. G01N 21/00
(52) U.S. Cl. ..................................................... 356/73.1
(58) Field of Search ....................... 356/73.1, 364–370; 385/15–18, 34, 24, 65, 73, 31, 46

(56) References Cited

U.S. PATENT DOCUMENTS 6,043,922 A * 3/2000 Koga et al. .................. 398/213
6,204,924 B1 * 3/2001 Cyr ............................. 356/453
6,211,957 B1 * 4/2001 Erdogan et al. ............. 356/364

* cited by examiner

Primary Examiner—Tu T. Nguyen
(74) Attorney, Agent, or Firm—Thomas Adams

(57) ABSTRACT

A property of a device that is dependent upon both wavelength and state of polarization is measured by; passing through the device an optical signal having its wavelength and SOP varied, the wavelength over a spectral range of the device and the SOP between four Mueller SOPs; measuring the insertion loss of the device for each of the four SOPS and at each wavelength; using the four insertion loss measurements for each of the four different states of polarization for each wavelength to compute the four elements of the first line of the Mueller matrix for each wavelength; and using the Mueller matrix elements, computing insertion loss variations for the device for a multiplicity of input states of polarization in addition to the four states of polarization for which the actual attenuation measurements were made and using the insertion loss variations to compute the polarization and wavelength dependent property.

22 Claims, 2 Drawing Sheets

MEASUREMENT OF OPTICAL PROPERTIES OF PASSIVE OPTICAL DEVICES USING THE MATRIX METHOD

This application claims priority from U.S. Provisional patent application No. 60/359,647 filed Feb. 27, 2002.

BACKGROUND OF THE INVENTION

1. Technical Field

The invention relates to a method and apparatus for measuring optical properties of passive optical devices in dependence upon both wavelength and polarization state using a so-called matrix method.

The invention is especially, but not exclusively, applicable to the measurement of polarization dependent center wavelength (PDCW) and polarization dependent bandwidth (PDBW).

2. Background Art

Polarization dependent properties of an optical device, such as polarization dependent loss (PDL), are measured by passing light through the device and measuring the output power while varying the state of polarization through a wide range of states of polarization. For accuracy, a large number of measurements are taken so as to cover most of the Poincaré sphere. The number of measurements may be reduced by using the so-called Mueller matrix method as disclosed in, for example, International Electrotechnic Commission standard IEC 61300-3-12 1997-02 and in U.S. Pat. No. 5,371,597 (Favin et al.), specifically by computing PDL by taking measurements with only four distinct states of polarization, one of which is elliptical, and computing only the four elements of the first row of the Mueller matrix. These four elements allow the output power to be computed for any input state of polarization. This reduces the number of measurements significantly.

It is desirable to be able to measure optical properties of an optical component over a range of wavelengths. More particularly, it is desirable to be able to measure polarization dependent center wavelength (PDCW) and polarization dependent bandwidth (PDBW) because, in DWDM systems, standards define wavelength ranges within which devices must operate. If PDBW is too large, there is an increased risk of crosstalk. If PDCW is too great, the wavelength could stray towards the end of the range. In either case, signal power would be compromised.

An object of the present invention is to provide a method and apparatus for effecting such optical property measurements efficiently.

SUMMARY OF THE INVENTION

According to one aspect of the present invention, a method of measuring a polarization and wavelength dependent property of an optical device comprises the steps of.

(i) passing through the device an optical signal and varying the wavelength of the optical signal over a wide range of wavelengths;

(ii) selecting four unique states of polarization of the optical signal, at least one of the unique states of polarization being elliptical;

(iii) measuring the optical signal leaving the device and determining the insertion loss of the device for each of the four states of polarization and at each wavelength;

(iv) using the four insertion loss measurements for each of the four different states of polarization at each wavelength to compute the four elements of the first line of the Mueller matrix for each wavelength; and (v) using the Mueller matrix elements, computing a set of insertion loss variations with wavelength for the device for each of a multiplicity of input states of polarization substantially covering the Poincaré sphere, and computing said polarization and wavelength dependent property from the computed sets of insertion loss variations.

Variation of the wavelength may be achieved by varying the wavelength of the optical signal before application to the device, or by using a broadband optical source and performing the measurements at each of a plurality of wavelengths in the range.

The step of computing said polarization and wavelength dependent property may include the steps of selecting two sets of insertion loss variations exhibiting the maximum bandwidth and minimum bandwidth, respectively, at a prescribed insertion loss and computing therefrom a polarization dependent bandwidth (PDBW).

Additionally or alternatively, the step of computing said polarization and wavelength dependent property may include the steps of selecting the two insertion loss variations exhibiting the maximum and minimum center wavelength, respectively, and computing therefrom the polarization dependent center wavelength (PDCW).

The three unique states of polarization other than the elliptical state conveniently may comprise three substantially linear states of polarization.

The states of polarization may be selected by means of a polarization state adjustor before application to the device under test. Alternatively, they may be selected by means of a polarization state analyzer after the optical signal has passed through the device under test.

According to a second aspect of the invention, apparatus for measuring a polarization dependent property of an optical device comprises:

a tunable optical source for supplying an input optical signal to an optical device under test (DUT) and varying its wavelength over a wide range of wavelengths, or a broadband source for supplying the input optical signal to the DUT and a tunable measuring system for detecting the output optical signal and performing measurements over a prescribed range of wavelengths;

polarization state selection means for selecting four unique states of polarization of the optical signal, at least one of which is elliptical;

means for measuring the optical signal leaving the DUT to determine insertion loss of the DUT for each of said four polarization states at each of said wavelengths;

means for computing from the four measurements for each wavelength the four elements of the first line of the Mueller matrix, and, using the Mueller matrix elements, computing a set of insertion loss variations with wavelength for the device for each of a multiplicity of input states of polarization substantially covering the Poincaré sphere, and computing said polarization and wavelength dependent property from said sets of insertion loss variations.

The means for computing said polarization and wavelength dependent property may be arranged to select the two insertion loss variations exhibiting the maximum bandwidth and minimum bandwidth, respectively, at a prescribed insertion loss, for example, relative to the peak transmission, and compute therefrom a polarization dependent bandwidth (PDBW).

Additionally or alternatively, the computing means may be arranged to select the two insertion loss variations exhibiting the maximum and minimum center wavelength, respectively, and compute therefrom the polarization dependent center wavelength (PDCW).

The three unique states of polarization other than the elliptical state of polarization conveniently may comprise three substantially linear states of polarization.

The polarization state selection means may comprise a polarization state adjustment device for adjusting the state of polarization of the optical signal before application to a port to which, in use, the device under test will be connected. Alternatively, it may comprise a polarization state analyzer connected to a port which, in use, will be connected to receive the optical signal from the device under test.

The foregoing and other objects, features, aspects and advantages of the present invention will become more apparent from the following detailed description of a preferred embodiment of the invention, taken in conjunction with the accompanying drawings.

BRIEF DESCRIPTION OF THE DRAWINGS

An embodiment of the invention will now be described by way of example only and with reference to the accompanying drawings, in which.

DESCRIPTION OF THE PREFERRED EMBODIMENTS

The apparatus for measuring optical properties of a device under test (DUT) shown schematically in FIGS. 1A and 1B maybe a model EXFO IQ-12004 B DWDM Passive Component Test System equipped with a Polarization State Adjuster module IQ-5150, which is available from EXFO Electro-optical Engineering Ltd. of Quebec, Canada, with its built-in microprocessor programmed to perform the specific measurements described below.

Figure 1A:
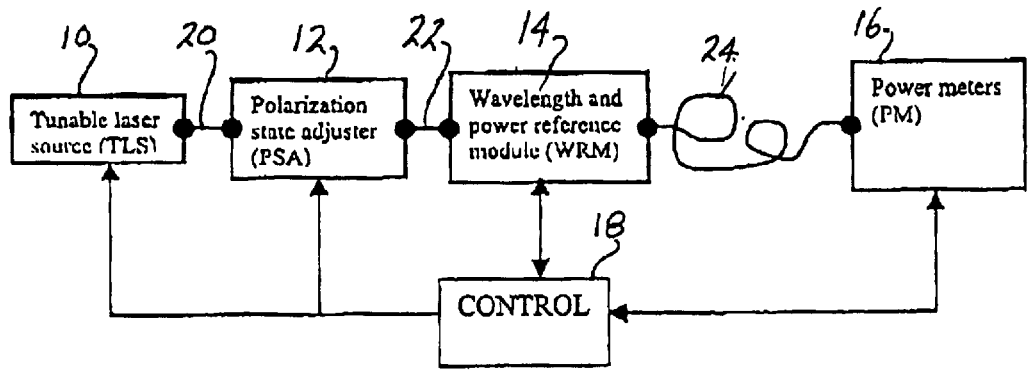
FIG. 1A is a block schematic diagram of an apparatus for measuring transmission curves of a device under test (DUT), without the DUT in place.

As shown in FIG. 1A, the apparatus comprises a tunable laser source (TLS) 10, a polarization adjustment unit (PSA) 12, a wavelength and power reference module (WRM) 14, a power meter 16 and a control unit 18, conveniently a microprocessor. An output port of the tunable laser source 10 is coupled to an input port of the polarization state adjustment unit by a first single mode optical fiber 20 and an output port of the latter is connected to an input port of the wavelength and power reference module 14 by a second single mode optical fiber 22. The control unit 18 is connected to the other three components to control the tunable laser source 10 and the polarization state adjustment unit 12 and to both control and monitor the wavelength and power reference unit 14 and the power meter 16.

The tunable laser source 10 supplies a polarized optical signal having a low spectral width to the polarization state adjustment unit (PSA) 12 which selects, sequentially, a set of "Mueller" SOPs, i.e., three states of polarization that are linear and one state of polarization that is not linear. Typically, but not necessarily, the four SOPs comprise three linear states of polarization (SOPs) at 0°, 45° and 90°, respectively, and one elliptical SOP (e.g., nearly circular).

The wavelength and power reference (WRM unit 14 includes wavelength references and an internal optical power meter for power referencing to ensure that the measurements taken at the various wavelengths and states of polarization are accurate.

An input port of the external power meter unit 16 is coupled to an output port of the WRM unit 14 by an optical fiber patch cord 24.

The instrument usually will have been calibrated in during manufacture. Each time it is to be used for measuring, for example, the insertion loss of the DUT, however, the instrument is used to perform a "reference measurement" without the DUT in place, e.g., to obtain a reference insertion loss for the instrument. This entails the control unit 18 tuning the laser source 10 to vary the wavelength of the optical signal over a wide range of values for each of the four polarization states selected in turn by the PSA 12. Usually, the control unit 18 will select the SOP, cause the tunable laser source to vary the wavelength continuously over the normal operating range, and control the power meter unit 16 to sample the output power of the light from the optical fiber patch cord 24 at intervals (e.g., every 5 or 10 picometers) throughout the range of wavelengths. (It would be possible to select each wavelength in turn and vary the SOP between the four SOPs, but that would be more time consuming.) This reference measurement is made on the first power meter channel only and is applied to each of the other channels (along with the relative wavelength response calibration for that channel). The reference measurement may be repeated as necessary.

The control unit 18 monitors the reference power readings taken at each wavelength and SOP by the power meter unit 16 and stores the data.

Figure 1B:
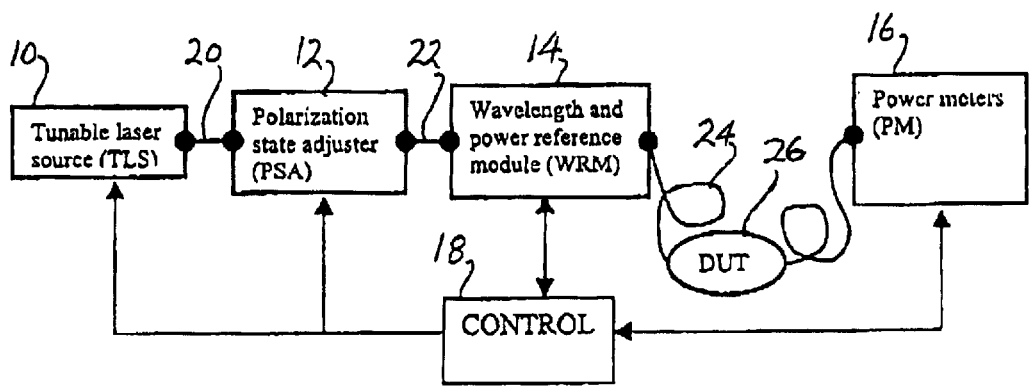
FIG. 1B is a block schematic diagram of the apparatus of FIG. 1A but with the DUT in place.

Following the initial referencing process, the device under test (DUT) 26 is connected between the WRM 14 and the power meter unit 16, as shown in FIG. 1B. How the DUT 26 is connected to the power meter unit 16 will depend upon the number of its output ports and their type, e.g. for connectors or not. It will be appreciated that the power meter unit 16 will have as many input ports and channels as there are output ports of the DUT 26. Of course, if the DUT 26 has only one output port, it may advantageously be spliced into the patch cord 24.

The control unit 18 then repeats the measurements, i.e., varying the wavelength of the optical signal over a wide range of wavelengths of interest, e.g. over the spectral range of the DUT 26, for each of the four SOPs and storing the corresponding power measurements for each wavelength/SOP combination. Subtracting each reference power measurement (in dB) from the corresponding power measurements taken with the DUT 26 in place gives the insertion loss (in dB) of the DUT 26 at that wavelength and input SOP.

The number of wavelengths at which measurements or "samples" are taken for each SOP will be determined according to the accuracy required. Typically, however, the power meter 16 and control unit 18 might sample every 5 or 10 picometers.

From these insertion loss values for the four input SOPs for a given wavelength, the control unit 18 computes the four elements of the first line of the Mueller matrix. It should be noted that, although the four readings taken for each wavelength (one for each SOP) are used to compute each of the elements of the first row of the Mueller matrix, the four elements are not specific to those four SOPs but are generalized. Consequently, they may be used to compute insertion loss of the DUT 24 at other input SOPs. For more information about the computation of the first row of Mueller matrix elements, the reader is directed to the afore-mentioned U.S. Pat. No. 5,371,597 and IEC 61300-3-12 1997-02, which are incorporated herein by reference.

Having computed the first row of elements of the Mueller matrix for each of the wavelengths for which the power meter unit 16 took readings, the control unit 18 proceeds to use the Mueller matrix elements to compute "transmission curves", i.e., curves of insertion loss with respect to wavelength, for a multiplicity of additional input-SOPs (normalized Stokes vectors §), as follows:

For i=1 to n, where n is the number of wavelengths in the curve, $$T(\lambda_i) = \vec{M}(\lambda_i) \cdot \hat{S}$$

$$\vec{M}(\lambda_i) = \begin{pmatrix} M_{00}(\lambda_i) \\ M_{01}(\lambda_i) \\ M_{02}(\lambda_i) \\ M_{03}(\lambda_i) \end{pmatrix} \quad \hat{S} = \begin{pmatrix} 1 \\ S_1 \\ S_2 \\ S_3 \end{pmatrix} = \begin{pmatrix} 1 \\ \cos(\psi)\cos(\phi) \\ \cos(\psi)\sin(\phi) \\ \sin(\psi) \end{pmatrix}$$

$$T(\lambda_i) = M_{00}(\lambda_i) + M_{01}(\lambda_i)\cos\psi\cos\phi + M_{02}(\lambda_i)\cos\psi\sin\phi + M_{03}(\lambda_i)\sin\psi$$

This is done for a set of parameter pairs ($\phi$,$\psi$), with $\phi$ going from 0 to $2\pi$ and $\psi$ going from $-\pi/2$ to $\pi/2$ to cover the Poincarré sphere. The number of parameter pairs (or the number of curves) will determine the accuracy of the procedure. A less complete coverage of the sphere will be faster but less accurate than a more complete coverage.

Covering the sphere might not be necessary if a priori knowledge of the DUT allows it to be modelled and if this model gives the parameter pairs ($\phi$, $\psi$) for the axes of the maximum and minimum optical property directly from the measured four states (e.g. the PDL axes, if they do not vary with wavelength). It is important to note, however, that this would not be a general method, but would give an approximate value whose accuracy depended upon how well the model applied.

Calibrations must also be taken into account, such as input-SOP as a function of wavelength and detector sensitivity as a function of wavelength. Such calibration will usually be carried out at regular intervals in a conventional manner and will not be described further herein.

Figure 2A:
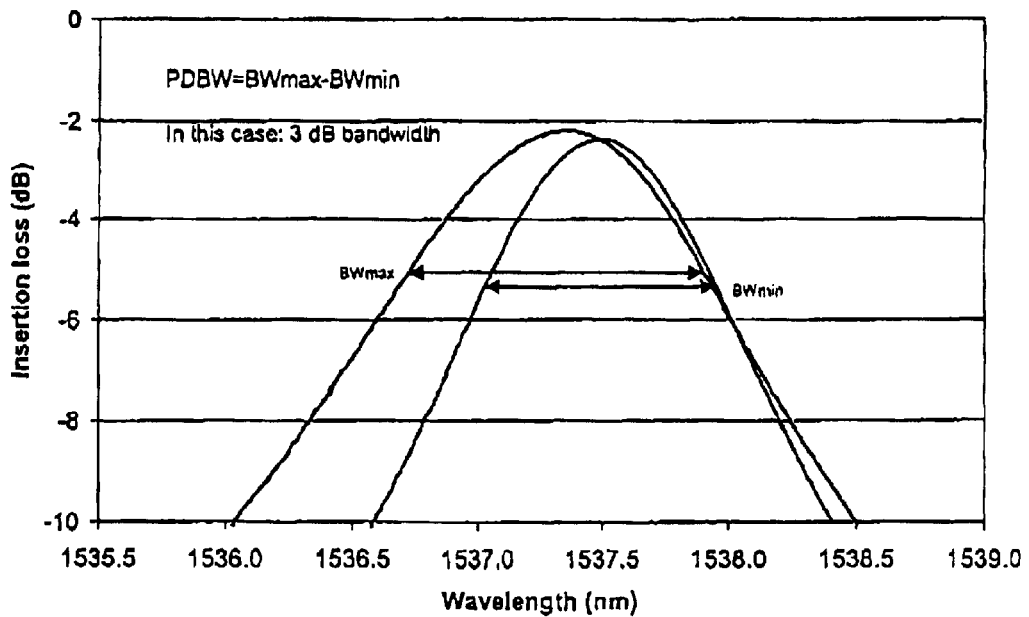
FIG. 2A illustrates two of a multiplicity of curves each showing variation of insertion loss with wavelength, one corresponding to maximum bandwidth and the other corresponding to minimum bandwidth, and shows derivation of PDBW therefrom.
Figure 2B:
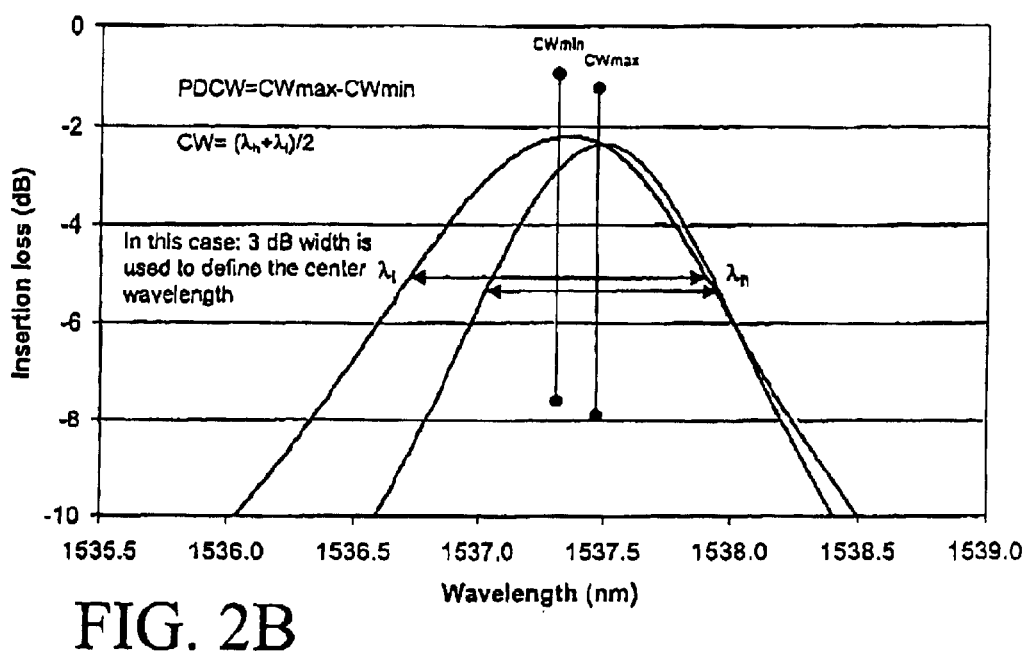
FIG. 2B illustrates similar curves but for maximum and minimum center wavelength, and shows the derivation of PDCW.

The insertion loss variation curves for a multiplicity of input-SOP's, i.e., covering the Poincaré sphere, are computed and used to determine the center wavelengths (CW) and bandwidths (BW), which allows the maximum center wavelength ($CW_{max}$) or bandwidth ($BW_{max}$) and the minimum center wavelength ($CW_{min}$) or bandwidth ($BW_{min}$) to be computed. In the examples shown in FIGS. 2A and 2B, in both cases, the insertion loss at which the attributes $CW_{min}$, $CW_{max}$, $BW_{min}$, and $BW_{max}$ are measured is the 3 dB width. Then:

$$PDCW = CW_{max} - CW_{min}$$

$$CW = (\lambda_H + \lambda_L)/2$$

and $PDBW = BW_{max} - BW_{min}$ i.e., the 3 dB bandwidth.

An advantage of embodiments of the present invention is that, once the four elements of the first row of the Mueller matrix have been obtained, the transmission curves for the DUT 24 can be reconstructed for any input-SOP without the need for any other actual measurements.

Although the above-described preferred embodiment of the invention is for computing PDCW and PDBW, it should be appreciated that the invention is applicable to the measurement of any attribute which can be deduced from the (optical) power transmission curves with respect to wavelength and polarization.

It is envisaged that the tunable optical source 10 could be unpolarized and the PSA 12 could be omitted, the selection of the four states of polarization then being provided by a polarization state analyzer connected between the DUT 24 and the power meter unit 16.

It is also envisaged that the tunable optical source could be replaced by a broadband source and the measuring system be tunable to each of the different wavelengths at which the four insertion losses for the four polarization states are to be measured.

Although an embodiment of the invention has been described and illustrated in detail, it is to be clearly understood that the same is by way of illustration and example only and not to be taken by way of the limitation, the spirit and scope of the present invention being limited only by the appended claims.

What is claimed is:

1. A method of measuring a polarization and wavelength dependent property of an optical device comprising the steps of:
   (i) passing an optical signal through the device;
   (ii) selecting four unique states of polarization of the optical signal, at least one of the unique states of polarization being elliptical;
   (iii) measuring the optical signal leaving the device and determining the insertion loss of the device for each of the four states of polarization and at each of a plurality of wavelength of the optical signals;
   (iv) using the four insertion loss measurements for each of the four different states of polarization at each wavelength to compute the four elements of the first line of the Mueller matrix for each wavelength; and
   (v) using the Mueller matrix elements, computing a set of insertion loss variations with wavelength for the device for each of a multiplicity of input states of polarization substantially covering the Poincaré sphere, and computing said polarization and wavelength dependent property from the computed sets of insertion loss variations.

2. A method according to claim 1, wherein the wavelength of the optical signal is varied before passing it through the device.

3. A method according to claim 1, wherein the optical signal is supplied by a broadband source and the measurement of the optical signal leaving the device is performed at each of said plurality of wavelengths.

4. A method according to claim 1, wherein the step of computing said polarization and wavelength dependent property includes the steps of selecting the two sets of insertion loss variations exhibiting the maximum bandwidth ($BW_{MAX}$) and minimum bandwidth ($BW_{MIN}$), respectively, at a prescribed insertion loss, and computing therefrom a polarization dependent bandwidth (PDBW).

5. A method according to claim 4, wherein the four unique states of polarization comprise three linear states of polarization.

6. A method according to claim 1, wherein the step of computing said polarization and wavelength dependent property includes the steps of selecting two sets of insertion loss variations curves exhibiting the maximum bandwidth ($BW_{MAX}$) and minimum bandwidth ($BW_{MIN}$), respectively, at a prescribed insertion loss, and computing therefrom a polarization dependent bandwidth (PDBW), and the steps of selecting the two sets of insertion loss variations exhibiting the maximum center wavelength ($CW_{MAX}$) and minimum center wavelength ($CW_{MIN}$), respectively, and computing therefrom the polarization dependent center wavelength (PDCW).

7. A method according to claim 1, wherein the four unique states of polarization comprise three linear states of polarization.

8. A method according to claim 1, wherein the step of computing said polarization and wavelength dependent property includes the steps of selecting two sets of insertion loss variations exhibiting the maximum center wavelength ($CW_{MAX}$) and minimum center wavelength ($CW_{MIN}$), respectively, and computing therefrom the polarization dependent center wavelength (PDCW).

9. A method according to claim 8, wherein the four unique states of polarization comprise three linear states of polarization.

10. A method according to claim 1, wherein the states of polarization are selected by means of a polarization state adjustor before application to the device under test.

11. A method according to claim 1, wherein the states of polarization are selected by means of a polarization state analyzer after the optical signal has passed through the device under test.

12. Apparatus for measuring a polarization dependent property of an optical device comprising:
   an optical source for supplying an input optical signal to the optical device;
   polarization state selection means for selecting four unique states of polarization of the optical signal, at least one of which is elliptical;
   means for measuring the optical signal leaving the DUT to determine insertion loss of the DUT for each of said four polarization states at each of a plurality of wavelengths of the optical signal;
   means for computing from the four measurements for each wavelength the four elements of the first line of the Mueller matrix, and, using the Mueller matrix elements, computing a set of insertion loss variations with wavelength for the device for each of a multiplicity of input states of polarization substantially covering the Poincaré sphere, and computing said polarization and wavelength dependent property from said computed stet of insertion loss variations.

13. Apparatus according to claim 12, wherein the optical source is tunable over said plurality of wavelengths.

14. Apparatus according to claim 12, wherein the optical source is a broadband optical source and the measuring means is tunable to each of said plurality of wavelengths.

15. Apparatus according to claim 12, wherein the means for computing said polarization and wavelength dependent property is operable to select the two sets of insertion loss variations exhibiting the maximum bandwidth and minimum bandwidth, respectively, at a prescribed insertion loss and compute therefrom a polarization dependent bandwidth (PDBW).

16. Apparatus according to claim 12, wherein the computing means is operable to select two sets of insertion loss variations exhibiting the maximum and minimum center wavelength, respectively, and compute therefrom the polarization dependent center wavelength (PDCW).

17. Apparatus according to claim 12, wherein the means for computing said polarization and wavelength dependent property is operable to select two sets of insertion loss variations exhibiting the maximum bandwidth and minimum bandwidth, respectively, at a prescribed insertion loss and compute therefrom a polarization dependent bandwidth (PDBW) and to select the two insertion loss variations exhibiting the maximum and minimum center wavelength, respectively, and compute therefrom the polarization dependent center wavelength (PDCW).

18. Apparatus according to claim 12, wherein the four unique states of polarization comprise three substantially linear states of polarization.

19. Apparatus according to claim 12, wherein the four unique states of polarization comprise three substantially linear states of polarization.

20. Apparatus according to claim 12, wherein the four unique states of polarization comprise three substantially linear states of polarization.

21. Apparatus according to claim 12, wherein the polarization state selection means comprises a polarization state adjustment device for adjusting the state of polarization of the optical signal before application to a port to which, in use, the device under test will be connected.

22. Apparatus according to claim 12, wherein the polarization state selection means comprises a polarization state analyzer connected to a port which, in use, will be connected to receive the optical signal from the device under test.

\* \* \* \* \*